United States Patent
Sato et al.

(10) Patent No.: US 8,109,150 B2
(45) Date of Patent: Feb. 7, 2012

(54) CRACK-PROPAGATION PREDICTION METHOD AND PROGRAM

(75) Inventors: Yoichi Sato, Hyogo (JP); Koichi Morimura, Hyogo (JP); Shinichiro Hori, Hyogo (JP); Shintaro Kumano, Hyogo (JP); Takanori Karato, Hyogo (JP); Masato Kurita, Hyogo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 333 days.

(21) Appl. No.: 12/530,394

(22) PCT Filed: Jul. 24, 2008

(86) PCT No.: PCT/JP2008/063237
§ 371 (c)(1),
(2), (4) Date: Sep. 8, 2009

(87) PCT Pub. No.: WO2009/017013
PCT Pub. Date: Feb. 5, 2009

(65) Prior Publication Data
US 2010/0116062 A1 May 13, 2010

(30) Foreign Application Priority Data
Jul. 27, 2007 (JP) ................................. 2007-195453

(51) Int. Cl.
*G01B 5/28* (2006.01)
*G06F 19/00* (2006.01)
*G01N 29/04* (2006.01)
*G01N 19/08* (2006.01)

(52) U.S. Cl. .............. 73/799; 702/34; 702/35; 702/181; 702/184

(58) Field of Classification Search ............ 73/799; 702/34–35, 181–184
See application file for complete search history.

(56) References Cited

U.S. PATENT DOCUMENTS
3,636,441 A * 1/1972 Fujimura et al. .............. 324/718
(Continued)

FOREIGN PATENT DOCUMENTS
JP 09-195795 A 7/1997
(Continued)

OTHER PUBLICATIONS
Korean Office Action dated Jun. 17, 2011, issued in corresponding Korean Patent Application No. 2009-7020255.
International Search Report of PCT/JP2008/063237, Mailing Date of Sep. 22, 2008.

*Primary Examiner* — Lisa Caputo
*Assistant Examiner* — Jonathan Dunlap
(74) *Attorney, Agent, or Firm* — Westerman, Hattori, Daniels & Adrian, LLP

(57) ABSTRACT

The precision of crack-propagation prediction is improved by taking into consideration a variation in the error due to inspectors and inspection methods. There is provided a crack-propagation prediction method including a correlation-information preparing step of measuring the length of a crack initiated in a test object by a plurality of inspectors and/or a plurality of inspection methods and obtaining correlation information between data acquired through the measurement and the condition of an actual crack; a crack-length estimating step of estimating the actual length of the crack initiated in an inspection target on the basis of the crack length measured by an inspector during inspection of the inspection target and the correlation information; and a crack-propagation-curve estimating step of estimating a crack-propagation curve of the inspection target originating from the crack length estimated in the crack-length estimating step.

9 Claims, 12 Drawing Sheets

U.S. PATENT DOCUMENTS

| | | | |
|---|---|---|---|
| 3,908,447 A * | 9/1975 | Salt | 73/799 |
| 4,764,882 A * | 8/1988 | Braschel et al. | 702/42 |
| 5,455,777 A * | 10/1995 | Fujiyama et al. | 702/34 |
| 6,289,739 B1 * | 9/2001 | Fujimoto et al. | 73/799 |
| 6,460,012 B1 * | 10/2002 | Welch et al. | 73/799 |
| 6,789,428 B2 * | 9/2004 | Nishimura et al. | 73/799 |
| 7,096,723 B2 | 8/2006 | Kienzle et al. | |
| 7,480,573 B2 * | 1/2009 | Toyosada | 702/34 |
| 2003/0200810 A1 * | 10/2003 | Nishimura et al. | 73/627 |
| 2004/0073400 A1 * | 4/2004 | Tomita et al. | 702/181 |
| 2009/0187353 A1 * | 7/2009 | Sakai et al. | 702/35 |
| 2009/0281735 A1 * | 11/2009 | Bechhoefer | 702/34 |

FOREIGN PATENT DOCUMENTS

| | | |
|---|---|---|
| JP | 10-160646 A | 6/1998 |
| JP | 2000-304731 A | 11/2000 |
| JP | 2002-156325 A | 5/2002 |
| JP | 2004-156580 A | 6/2004 |
| JP | 2004-516465 A | 6/2004 |
| JP | 2005-026250 A | 1/2005 |
| JP | 2007-256042 A | 10/2007 |
| KR | 2005-0078071 A | 8/2005 |
| WO | 02/50412 A1 | 6/2002 |

* cited by examiner

DISTRIBUTION a △ INSPECTOR X, INSPECTION METHOD A
DISTRIBUTION b ● INSPECTOR Y, INSPECTION METHOD A
DISTRIBUTION c × INSPECTOR X, INSPECTION METHOD B

○ ; MEASURED VALUE FROM INSPECTION
◉ ; ESTIMATED ACTUAL CRACK LENGTH

FIG. 9

| COMBINATION NO. | BOUNDARY CONDITION FACTOR | | | MATERIAL PROPERTY FACTOR | | | | | | SHAPE FACTOR |
|---|---|---|---|---|---|---|---|---|---|---|
| | HIGH-TEMPERATURE COMBUSTION GAS SIDE | | COOLING AIR | HEAT CONDUCTIVITY | HEAT EXPANSION COEFFICIENT | ... | FATIGUE CRACK INITIATION LIFE | | CRACK GROWTH RATE (FIRST) | | WALL THICKNESS | ... |
| | COMBUSTION GAS PRESSURE | HEAT TRANSFER COEFFICIENT | | | | | $\alpha$ | $C_i$ | $C_p$ | $m$ | | |
| 1 | 0.32 | 1.46 | ... | -0.80 | -0.39 | ... | 0.57 | -0.48 | -0.62 | 0.61 | -0.28 | ... |
| 2 | -1.84 | 0.40 | ... | 1.49 | 1.08 | ... | 0.47 | -0.66 | 0.76 | -0.79 | -0.97 | ... |
| 3 | 0.39 | 0.22 | ... | -0.13 | 0.69 | ... | -0.70 | 0.65 | -0.48 | 0.38 | -0.08 | ... |
| 4 | -2.11 | 0.55 | ... | -0.21 | 0.36 | ... | -0.48 | 0.92 | -0.71 | 0.75 | 1.22 | ... |
| 5 | 0.85 | 0.56 | ... | 1.42 | 0.18 | ... | -1.80 | 1.40 | 0.20 | 0.05 | -0.57 | ... |
| 6 | -1.24 | 0.83 | ... | -1.22 | 1.17 | ... | -0.49 | 0.09 | 1.07 | -1.14 | 0.89 | ... |
| 7 | -0.68 | -0.08 | ... | -1.73 | -0.38 | ... | 0.31 | -0.29 | 0.82 | -0.92 | 0.17 | ... |
| 8 | -0.90 | -0.15 | ... | 0.18 | 0.36 | ... | -0.13 | -0.08 | 1.32 | -1.33 | 0.16 | ... |
| ... | ... | ... | ... | ... | ... | ... | ... | ... | ... | ... | ... | ... |
| N | -088 | -0.43 | ... | 0.70 | 0.89 | ... | -0.92 | 0.55 | 0.69 | -0.70 | -0.63 | ... |

CRACK-PROPAGATION PREDICTION METHOD AND PROGRAM

TECHNICAL FIELD

The present invention relates to, for example, a crack-propagation prediction method and a program for predicting the propagation of the crack length of fatigue cracks initiated in parts used in high-temperature environments, such as gas turbines.

BACKGROUND ART

For example, combustor inner tubes, transition pieces, turbine rotor blades, stator vanes, shroud segments (ring segments), etc., which are hot-parts constituting a gas turbine, receive varying thermal stress due to starting up and stopping while being exposed to high-temperature, high-pressure combustion gas, and thus are easily damaged due to high-temperature fatigue, thermal fatigue, and creep. In particular, turbine rotor blades are severely damaged because they receive a centrifugal force due to rotor rotation and a gas bending force due to combustion gas; therefore, strict maintenance and management are required. Accordingly, an inspection schedule is set at appropriate intervals; during inspection, parts are removed for inspection if required, and the parts are replaced or repaired depending on the degree of damage.

It is desirable to set long intervals between periodic inspections because, while carrying out an inspection, costs are required for disassembling and examining the gas turbine apparatus, and electric power cannot be generated. Therefore, there is a need for improving the durability of hot-parts for gas turbine and setting appropriate intervals between periodic inspections. There is also a need for reducing the costs and time required for repairing damaged hot-parts. In order to achieve this, it is required to relax the repair criterion such that small cracks that will not cause damage to an extent that function will be lost by the time of the next periodic inspection are allowed to be left unrepaired.

To fulfill the above-described needs, it is necessary to precisely predict the propagation behavior of cracks formed in hot-parts. For predicting the crack length in hot-parts, as disclosed in, for example, Patent Document 1 and Patent Document 2, methods have been proposed for observing the maximum crack length, etc., of the used part, predicting the stress and temperature on the basis of the result, and predicting the fatigue life on the basis of a master curve acquired through the predicted values and a test piece.

Patent Document 1:
Japanese Unexamined Patent Application, Publication No. HEI-10-160646
Non-Patent Document 1:
Japanese Unexamined Patent Application, Publication No. HEI-9-195795

DISCLOSURE OF INVENTION

However, as described in the methods disclosed in the above-mentioned Patent Documents 1 and 2, there are the following problems in predicting the propagation behavior of a crack on the basis of the maximum crack-length measurement result of the hot-parts used.

The first problem is that crack propagation behavior in hot-parts is highly variable. This is thought to be due to many influencing factors that include practically unavoidable variation. Influencing factors include the temperature and heat transfer coefficients of high-temperature combustion gas and cooling air, which are environmental factors of hot-Parts; heat conductivity and heat expansion coefficients, which are material property factors, in particular, material parameters that define the fatigue crack initiation life (relationship between cyclic stress and crack initiation life) and crack-propagation rate, which are material-strength property parameters; and furthermore, dimensional tolerances, such as wall thickness, which are shape factors. Therefore, the data about maximum crack length or maximum crack-propagation rate actually measured in hot parts used for operating a gas turbine cannot be used for predicting crack propagation behavior when operating hot parts having a different specification or when the operating conditions are changed.

The second problem is a problem associated with the handling of the crack length measured during a periodic inspection. It has been apparent during a preliminary study conducted by the inventors that, when a crack is small, the magnitude of the detection limit differs depending on the type of inspection method and the skill of the inspector (for example, years of experience, proficiency, etc.) and that the measured values vary greatly. Therefore, when predicting the crack length during subsequent periodic inspections on the basis of the current inspection result (measured values of the crack length), variation based on the current measurement error is added to the variation in the crack-propagation rate itself, as described above. Consequently, it is necessary to set a considerably large safety factor for the predicted value of the crack length of the next periodic inspection.

When the crack behavior of hot parts, from when hot parts are brand new to when they are discarded, are predicted through simulation by a computing device, whether or not repair is required and the repair method are determined on the basis of the crack length measured when reaching the number of starts and stops corresponding to periodic inspection. However, when the crack length measured during the inspection is used for determining this, it is expected that the results will differ greatly from when it is not used.

For the points mentioned above about the second problem, it is necessary to include a probabilistic method in the prediction method while taking into consideration measurement error of the crack length and faulty determination that occurs during inspection. However, so far, such a prediction method has not been disclosed.

The present invention has been conceived to solve the above-described problems, and it is an object thereof to provide a crack-propagation prediction method and program capable of improving the precision of crack-propagation prediction by taking into consideration a variation in the error due to inspectors and inspection methods.

To solve the above-described problems, the present invention provides the following solutions.

The present invention provides a crack-propagation prediction method including a correlation-information preparing step of measuring the length of a crack initiated in a test object by a plurality of inspectors and/or a plurality of inspection methods and obtaining correlation information between data acquired through the measurement and the condition of an actual crack; a crack-length estimating step of estimating the actual length of the crack initiated in the test object on the basis of the crack length measured by an inspector during inspection of an inspection target and the correlation information; and a crack-propagation-curve estimating step of estimating a crack-propagation curve of the inspection target originating from the crack length estimated in the crack-length estimating step.

According to such a method, in the correlation-information preparing step, the length of a crack initiated in a test object is measured by a plurality of inspectors and/or a plurality of inspection methods and correlation information between data acquired through the measurement and the condition of an actual crack is obtained, and, in the crack-length estimating step, the actual length of the crack initiated in the test object is estimated on the basis of the crack length measured by an inspector during inspection of an inspection target and the correlation information; therefore, it is possible to improve the precision of estimating the crack length that serves as the origin when estimating a crack-propagation curve. In this way, it is possible to improve the precision of estimating the crack-propagation curve. As a result, it is possible to specify, at high precision, the numerical value range of the actual crack length. According to the present invention, the crack-propagation curve is estimated by taking into consideration the measurement error due to the differences in the inspectors and the measurement error due to the differences in the inspection methods; therefore, it is possible to specify the numerical value range of the actual crack length with a margin that is neither too large nor too small.

An example of the test object is, for example, a test piece made of the same material, etc. as the inspection target or an actual object prepared for testing. This test object may be anything that can be used to acquire correlation information, such as the degree of error in a measurement of the condition of a crack initiated in the test object due to the differences in inspectors and/or inspection methods, and the shape, size, etc. are not limited.

In the crack-propagation prediction method described above, in the crack-propagation-curve estimating step, some or all parameters determining a crack initiation life and a crack-propagation rate for determining the relationship between the number of starts and stops after the inspection and the crack length may be set to contingent random variables, and the crack-propagation curve may be probabilistically predicted using a Monte Carlo Method.

In the crack-propagation prediction method described above, in the correlation-information preparing step, the correlation information may be prepared for each of the inspection methods and/or each measuring ability level of the inspectors, and in the crack-length estimating step, the actual crack length may be estimated using the correlation information corresponding to the inspection method used during the inspection and/or the measuring ability of the inspector who carried out the measurement during the inspection.

The variation in the error included in the measured values differs depending on the measuring ability (for example, proficiency, years of experience, etc.) of the inspector and the inspection method. Therefore, by determining the correlation between the measured values and the actual crack length for each inspector, each inspection method, or each combination of inspector and inspection method and by correcting the measured values from the inspection using the correlation corresponding to the inspector or inspection method of the actual inspection, it is possible to estimate the actual crack length with superior precision. In this way, the crack propagation curve can be estimated accurately.

The present invention provides a crack-propagation prediction method for predicting a time-sequential change in the length of a crack initiated in an inspection target by simulating the conditions of the inspection target from the beginning of use, the method including a first crack-propagation-curve estimating step of estimating a crack-propagation curve from the beginning of use of the inspection target; a correlation-information preparing step of measuring the length of the crack initiated in a test object by a plurality of inspectors or a plurality of inspection methods and obtaining correlation information between data acquired through the measurement and the condition of an actual crack; a predicted-measured-value calculating step of calculating a predicted measured value by using the correlation information to correct an actual crack length obtained during inspection predicted in the first crack-propagation-curve estimating step; and an actual-crack-length changing step of determining whether or not the predicted measured value is equal to or smaller than a repair criterion set in advance and changing, in response to the determination result, the actual crack length obtained during the inspection.

According to such a method, the length of a crack initiated in a test object is measured by a plurality of inspectors and/or a plurality of inspection methods and correlation information between data acquired through the measurement and the condition of an actual crack is obtained, and a predicted measured value is estimated on the basis of the actual crack length of the inspection target obtained, during the inspection in the first crack-propagation-curve estimating step; therefore, it is possible to set the predicted measured value close to the values measured by the inspector during the actual inspection. Then, the predicted measured value obtained during the inspection is changed depending on whether or not the predicted measured value is smaller than or equal to the repair criterion; therefore, it is possible to carry out simulation according to actual operation.

In this way, according to the present invention, the predicted measured value is estimated by taking into consideration the measurement error due to the differences in the inspectors and the measurement error due to the differences in the inspection methods; therefore, it is possible to improve the simulation precision. Furthermore, by calculating the condition of the crack propagation and the repair cost when the repair criterion is changed, a repair criterion that minimizes costs can be determined.

In crack-propagation prediction method described above, in the actual-crack-length changing step, when the predicted measured value obtained during the inspection exceeds the repair criterion, the crack is to be repaired, and the actual crack length may be changed to a value equal to zero or smaller than the original length.

In crack-propagation prediction method described above, the second crack-propagation-curve estimating step may further include a second crack-propagation-curve estimating step of estimating a crack-propagation curve originating from the actual crack length when the predicted measured value is equal to or smaller than the repair criterion.

In crack-propagation prediction method described above, in at least one of the first crack-propagation-curve estimating step and the second crack-propagation-curve estimating step, some or all parameters determining a crack initiation life and a crack-propagation rate for determining the relationship between the number of starts and stops and the crack length may be set to contingent random variables, and the crack-propagation curve may be probabilistically predicted using a Monte Carlo Method.

The present invention provides a crack-propagation prediction program causing a computer to execute a step of obtaining correlation information between data of the length of a crack initiated in a test object measured by a plurality of inspectors and/or a plurality of inspection methods and an actual crack length; a step of estimating the actual length of a crack initiated in an inspection target on the basis of the crack length measured by an inspector during inspection of the inspection target and the correlation information; and a step of estimating a crack-propagation curve of the inspection target originating from the estimated crack length.

The present invention provides a crack-propagation prediction program for predicting a time-sequential change in the length of a crack initiated in an inspection target by simulating the conditions of the inspection target from the beginning of use, the program causing a computer to execute a step of estimating a crack-propagation curve from the beginning of use of the inspection target; a step of obtaining correlation information between data of the length of a crack initiated in a test object measured by a plurality of inspectors and/or a plurality of inspection methods and an actual crack length; a step of calculating a predicted measured value by correcting an actual crack length in the inspection target obtained during inspection predicted in the step of estimating a crack-propagation curve, using the correlation information; and a step of determining whether or not the predicted measured value is equal to or smaller than a repair criterion set in advance and changing the actual crack length obtained during the inspection in response to the determination result.

According to the present invention, since the statistical variation in the crack-propagation behavior that may occur due to overlooking a crack during inspection or due to measurement error of the crack length can be taken into consideration, it is possible to improve the precision of crack-propagation prediction. In this way, the repair criterion can be prevented from being set with a too large or too small safety margin, and thus it is possible to realize a balance between repair cost reduction and strength reliability improvement.

Furthermore, the crack-propagation prediction method and program according to the present invention can be used for, for example, a part in which a crack forms and are suitable for use in predicting the propagation of a crack initiated in a part of a mechanical structure used in a high-temperature environment, such as a gas turbine.

The present invention has an advantage in that the precision of crack propagation prediction can be improved.

BRIEF DESCRIPTION OF DRAWINGS

FIG. 9 illustrates N combinations of parameters for acquiring crack-propagation curves.

EXPLANATION OF REFERENCE SIGNS

1: CPU
2: memory
3: hard disk
4: input device
5: monitor
6: CDD
7: bus line

BEST MODE FOR CARRYING OUT THE INVENTION

Embodiments of a crack-propagation prediction method, apparatus, and program according to the present invention will be described below with reference to the drawings. This embodiment describes a case in which the crack-propagation prediction method, etc. according to the present invention is applied to propagation prediction of a crack generated in a turbine rotor blade, which is the inspection target, in an extremely high-temperature environment in gas turbine equipment.

First Embodiment

Figure 1:
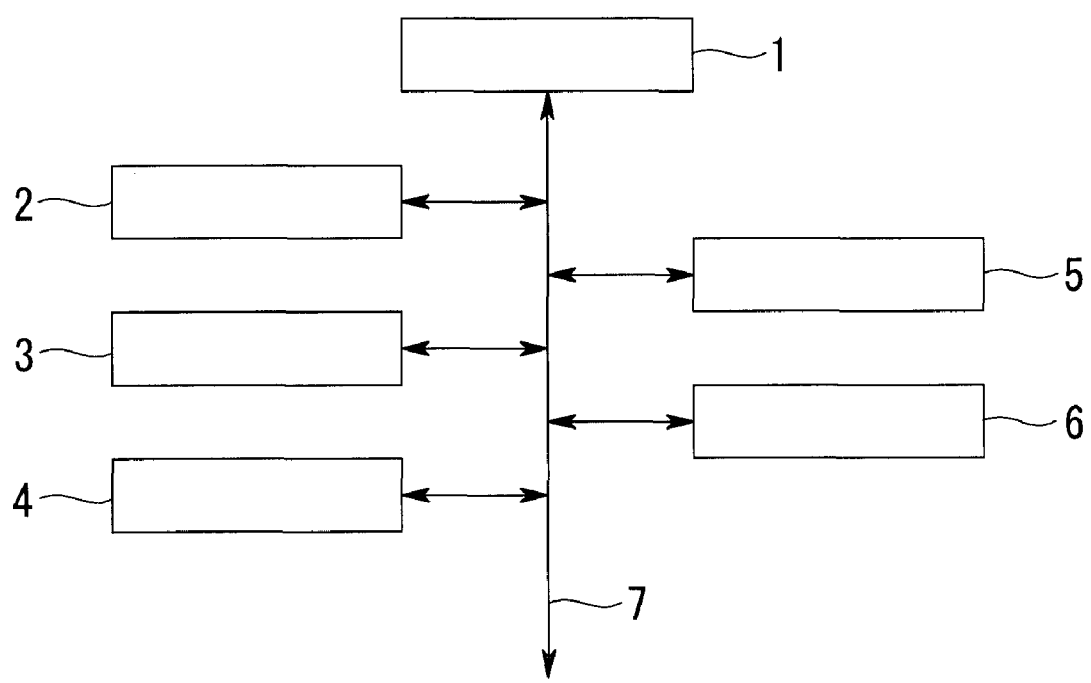
FIG. 1 illustrates the hardware configuration of a crack-propagation determining apparatus according to a first embodiment of the present invention.

FIG. 1 is a block diagram illustrating an example hardware configuration of a crack-propagation prediction apparatus according to a first embodiment of the present invention. As shown in FIG. 1, the crack-propagation prediction apparatus according to this embodiment is a computer system including a CPU (central processing unit) 1, a memory 2, a hard disk 3, an input device 4, a monitor 5, and a CDD (CD-ROM drive) 6. These components are connected via a bus line 7. The CPU 1 controls each unit via the bus line 7 according to respective programs stored in the hard disk 3.

A crack-propagation prediction program stored in the hard disk 3 is, for example, read out via the CDD 6 from a CD-ROM (not shown) in which the crack-propagation prediction program is stored and is installed on the hard disk 3. In addition to a CD-ROM, a program in a flexible disk (FD), an IC card, and so on may be installed from a computer-readable recording medium to a hard disk. Furthermore, the program may be downloaded using a communication line.

Next, a crack-propagation prediction method realized by the crack-propagation prediction apparatus having the above-described configuration will be described with reference to FIG. 2.

The crack-propagation prediction method described below is realized by the CPU 1, which is included in the crack-propagation prediction apparatus, reading out and executing the crack-propagation prediction program stored on the hard disk 3.

Figure 2:
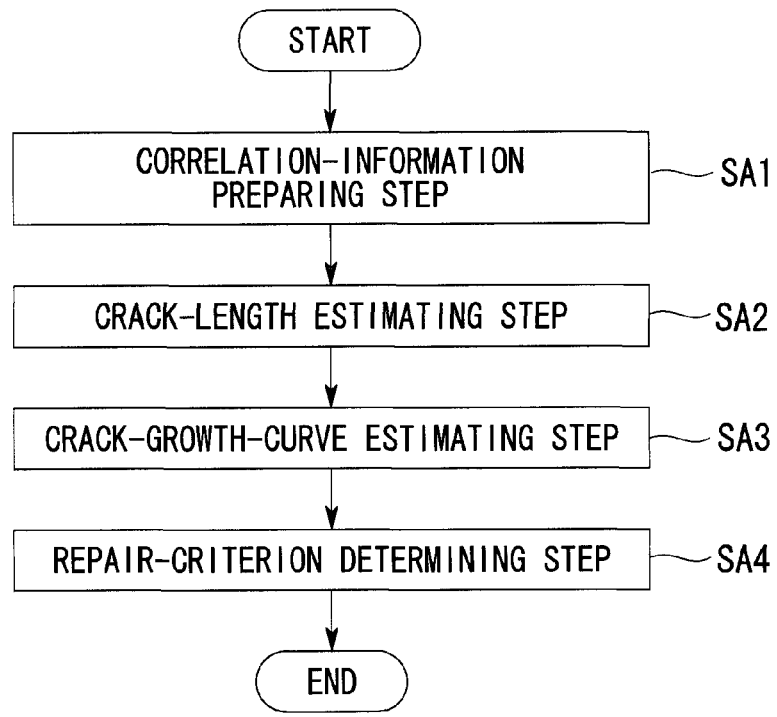
FIG. 2 is a flow chart illustrating a crack-propagation prediction method according to the first embodiment of the present invention.

As shown in FIG. 2, the crack-propagation prediction method includes a correlation-information preparing step (Step SA1) of measuring the length of a crack initiated in a test object by a plurality of inspectors or a plurality of examining methods and determining the correlation information between the data acquired through the measurement and the actual crack condition; a crack-length estimating step (Step SA2) of estimating the actual crack length on the basis of the crack length measured by an inspector during inspection of an inspection target and the correlation information; a crack-propagation-curve estimating step (Step SA3) of estimating crack-propagation curves originating from the crack length estimated in the crack-length estimating step; and a repair-criterion determining step (Step SA4) of determining an optimal repair criterion on the basis of the crack-propagation curves.

Here, examples of the correlation information include, as described below, a correlation between the crack lengths acquired by measurement and the actual crack length or the relationship between the crack lengths acquired by measurement and the probability of detecting the crack.

Each step will be described in detail below.

Correlation-Information Preparing Step

For example, in this step, a simulated inspection is first carried out separately from the actual inspection, and the correlation information is obtained on the basis of the measurement result acquired through this simulated inspection.

Figure 3:
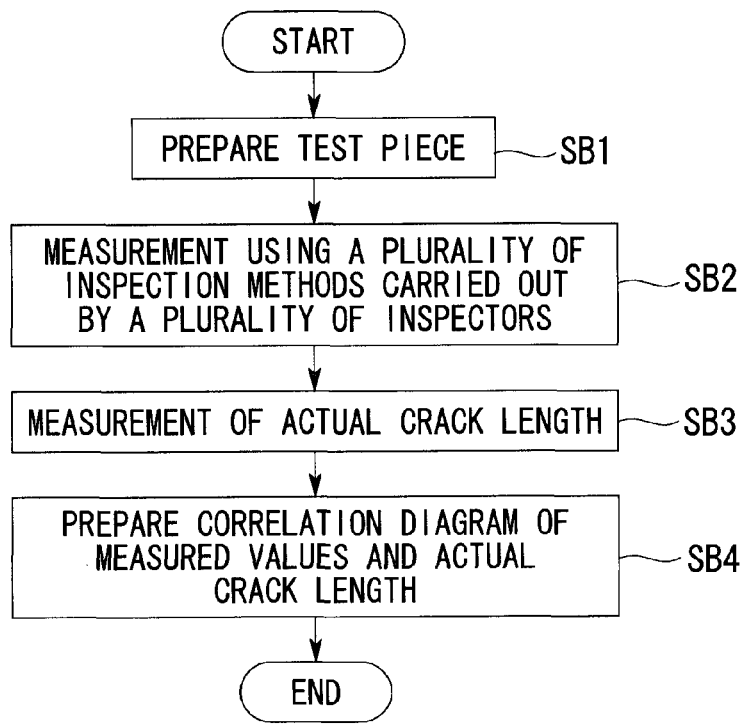
FIG. 3 is a flow chart illustrating a correlation-information preparing step shown in FIG. 2.

First, a test object to be used in the simulated inspection is provided (Step SB1 in FIG. 3). The test object is preferably a test piece or the like that simulates, as accurately as possible, the local shape and surface condition of the site to be examined so that obstacles and difficulties in actual inspection and factors causing measurement error are reproduced. It is necessary to introduce cracks to these before use/operation in the actual apparatus or by other methods (for example, repeatedly applying mechanical or thermal stress). At this time, for the purpose of the simulated inspection, it is preferable to introduce many cracks having various forms, i.e., crack depth, crack length, and condition of the crack opening. Here, the conditions of the crack opening are, for example, black scale, scale, and coarseness due to processing.

Instead of the test piece, an actual part used for actual operation and cracked as a result, or a test piece cut out from the actual part may be used as the test object.

Next, an inspector actually carrying out the inspection measures a crack initiated in the test object (Step SB2 in FIG. 3).

For example, if several inspectors alternately carry out the actual inspection, it is preferable that crack measurement be carried out by all of these inspectors conducting inspection. In this way, by carrying out crack measurement by all inspectors who may possibly be involved with the inspection, the measurement error of each inspector can be acquired as data. Furthermore, the inspectors measure a crack in the test object according to an inspection method applicable to the actual inspection. For example, they detect the crack and measure the crack length by visual checking, magnetic particle testing, ultrasonic testing, dye penetrant testing, fluorescent penetration testing, and so on, after carrying out pre-processing, such as surface cleaning, in the same way as in the actual inspection.

In this way, after the measurement by the inspectors ends, the actual crack length in the test object is measured (Step SB3 in FIG. 3).

Here, the "actual crack length" is ideally the true length that does not depend on the inspection and measurement means; however, it is acquired in practice through, for example, the following methods. For example, the cracked section is cut out or transferred into a replica from the test object, and the crack length is measured at high magnifying power using an optical microscope, a scanning electron microscope, a scanning tunnel microscope, or an atomic force microscope. Alternatively, the fracture surface is exposed in the test object, and the fracture surface shape can be measured with the microscope to obtain the crack length. In this way, in this step, the crack length is measured through a measurement method that enables a measurement precision higher than the measurement precision of a conventional inspection/measurement method applied on site in an actual plant.

The "actual crack length" is equivalent to a length that is mechanically valid or, in other words, a length for deriving a parameter that is appropriate for the calculation of crack propagation, such as a K value or a J integral. There are many factors causing differences between the actual length and the measured values. However, some main factors are the small opening of the end section of the crack and the difficulty of determining the end of the crack depending on the surface condition (surface scale, processing damage, etc.)

In this way, upon completion of measurement by each inspector and measurement of the actual crack length, these measured values are input via the input device 4 (see FIG. 1). At this time, the values measured by the inspectors are linked to the identification numbers of the test objects, the inspection methods, the IDs of the inspectors, etc. and then input. The actual crack length of each test object is linked to the ID of the test object and then input.

The input data is stored in a storage device, such as the hard disk 3.

Once input processing of the measured data of the simulated inspection is completed, a correlation diagram of the measured data, which is defined by combinations of inspectors and inspection methods using the measured data stored in the hard disk 3, and the actual crack length is prepared (Step SB4 in FIG. 3).

Figure 4:
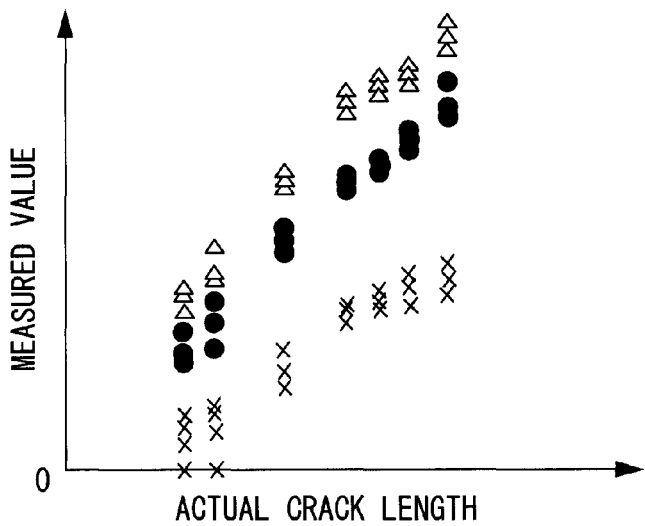
FIG. 4 illustrates an example correlation diagram prepared in the correlation-information preparing step shown in FIG. 2.

FIG. 4 illustrates an example correlation diagram. In FIG. 4, the horizontal axis is the actual crack length, and the vertical axis is the measured crack length; distribution a corresponds to the crack length measured by inspector X employing inspection method A; distribution b corresponds to the crack length measured by inspector Y employing inspection method A; and distribution c corresponds to the crack length measured by inspector X employing inspection method B. Here, only three examples are shown. However, the above-described distribution is prepared for each of the combinations of inspectors and inspection methods used in the simulated inspection.

In this way, by providing a correlation diagram corresponding to the inspector and inspection method, it is possible to accurately determine the degree of variation in the measurement error caused by the differences in the inspectors and the differences in the inspection methods. The measurement distribution prepared here is stored in the hard disk 3 and is referred to during the next inspection.

Crack-Length Estimating Step

Next, the crack-length estimating step will be described.

When the time for a periodic inspection arrives and the actual inspection is carried out, information about the measured values from the actual inspection, the inspectors, and the inspection methods is input via the input device 4 (see FIG. 1). The information items are linked and stored in the hard disk 3, and a correlation diagram linking the inspectors and the inspection methods is read out from the hard disk 3.

Figure 5:
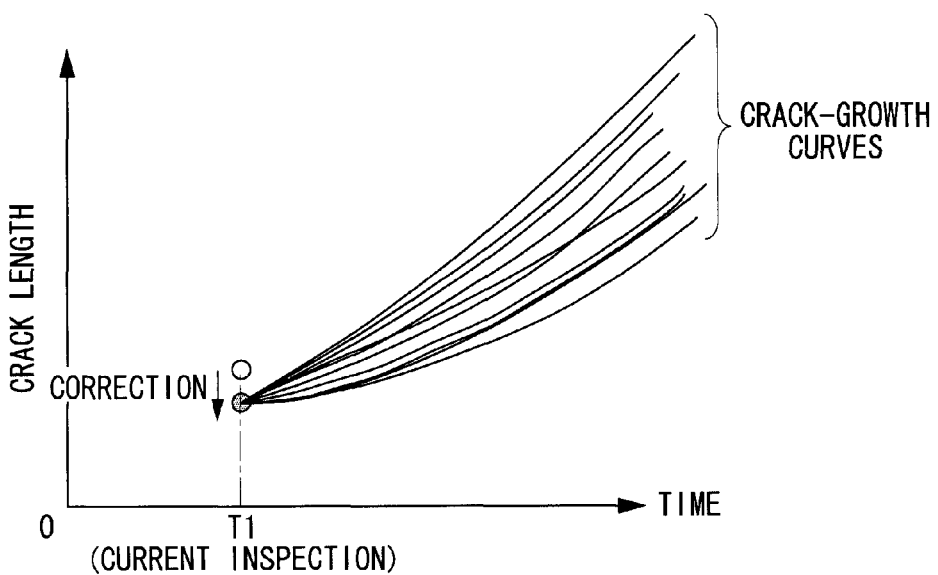
FIG. 5 illustrates an example crack-propagation curve estimated in a crack-propagation-curve estimating step shown in FIG. 2.

Subsequently, the read-out correlation diagram is used to estimate the actual crack length. Specifically, since the correlation of the measured values and the actual crack length is determined from the correlation diagram, the actual crack length is estimated by correcting the measured values obtained through the current inspection on the basis of the correlation. Instead, the probability distribution of the actual crack length with respect to a measured value may be determined from the correlation diagram, and the probability distribution of the actual crack length is estimated using this probability distribution (see FIG. 5). Here, FIG. 5 illustrates a case in which the crack length measured during an inspection is larger than the actual crack length. The estimated actual crack length has a distribution corresponding to the probability distribution calculated on the basis of FIG. 4. However, to simplify the description, it is represented by one point (definite value) in FIG. 5.

Crack-Propagation-Curve Estimating Step

In this step, a crack-propagation curve for after the inspection, originating from the actual crack length estimated in the crack-length estimating step, is calculated.

At this time, for influencing factors having an influence on the crack propagation and the crack-propagation rate, a probability distribution of the crack-propagation curves is determined by a Monte Carlo method. For example, all or some of the factors that influence the fatigue properties, such as material properties and their parameters, environmental factors, and shape parameters of members, are defined as influencing factors; the values of the influencing factors are determined on the basis of statistical data of these influencing factors; many combinations (for example, N combinations shown in FIG. 9) of these influencing factors are created; and the crack-propagation curves are calculated using data sets of the respective combinations. It is preferable that the number of combinations (for example, N sets in FIG. 9) be as large as possible.

As a result, for example, as shown in FIG. 5, many crack-propagation curves that take into consideration various influencing factors are acquired.

Repair-Criterion Determining Step

In this step, the probability distribution of the crack length is determined by statistically processing the multiple crack-propagation curves obtained in the crack-propagation-curve estimating step, and a repair criterion is determined on the basis of this probability distribution. A repair criterion is a criterion for determining how to treat a defect detected through inspection. Specifically, it is the dimensional lower limit at which it is determined that some treatment, such as removal of the defect or welding repair, is required. In the present invention, an allowable crack length Acr will be described as a specific example of a repair criterion.

Here, the allowable crack length Acr is the crack length when, if operation were to be resumed without repairing a crack having a length larger than or equal to the allowable crack length Acr, the crack would grow larger than or equal to a limit length (hereinafter referred to as "limit crack length Amax") at which hot parts are expected to fail before the next inspection. Here, "failure" includes not only destruction but also a condition in which a structural body does not provide its required function although it appears to be undamaged.

Figure 6:
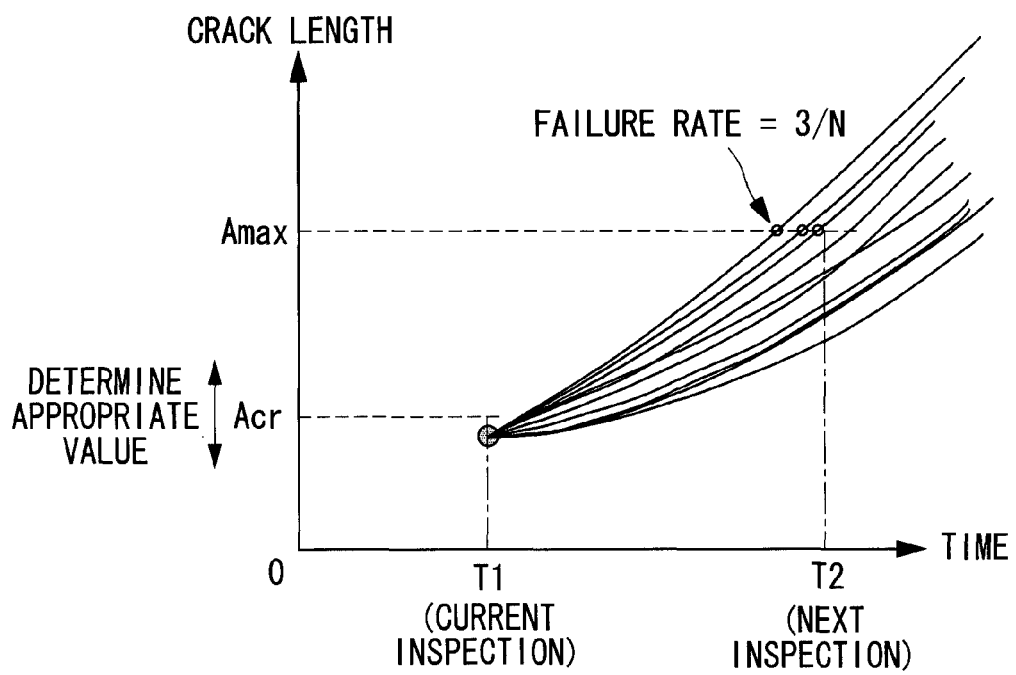
FIG. 6 illustrates the determination of a repair criterion.

First, as shown in FIG. 6, the crack length of some of the N crack-propagation curves obtained in the crack-propagation-curve estimating step may reach the limit crack length Amax when the number of starts and stops reaches a number equivalent to the next periodic inspection. The percentage of the crack-propagation curves that are larger than or equal to the limit crack length Amax with respect to all N curves (hereinafter referred to as "failure rate") depends on the actual crack length. Thus, when the allowable crack length Acr is appropriately set and a crack having a length larger than or equal thereto is found, failure can be prevented from occurring by repairing the crack such that the actual crack length becomes zero or smaller than the original length.

Figure 18:
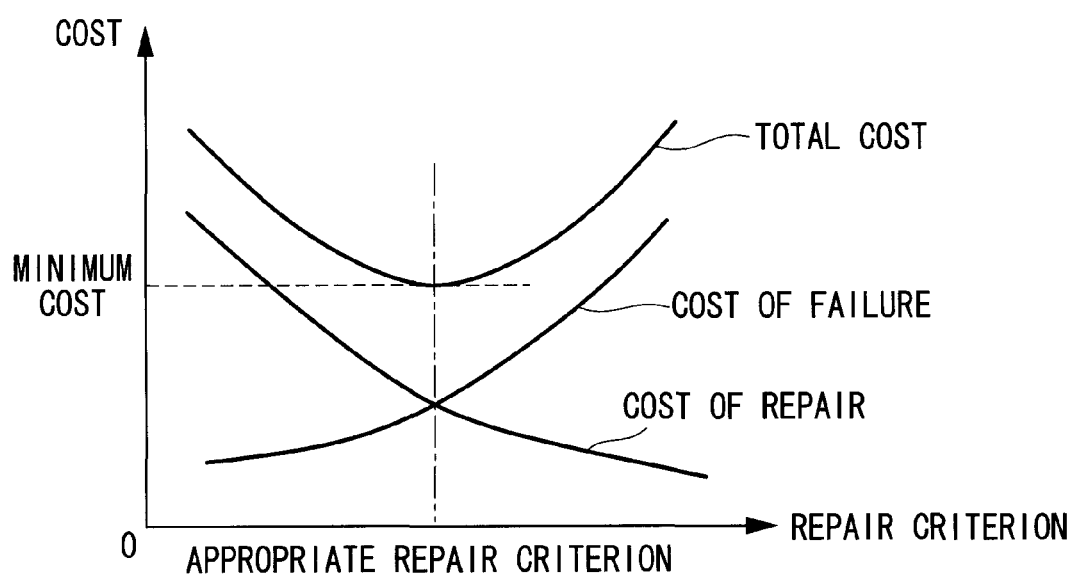
FIG. 18 illustrates a method of determining an optimal repair criterion.

Here, to completely prevent failure, the allowable crack length Acr must be set to a very small value. As a result, small cracks that actually do not require repair will be repaired, increasing the cost of repair. Therefore, as shown in FIG. 18, it is preferable to set an appropriate repair criterion that lowers the total cost, which is the sum of the cost of repair and the cost due to damage, such as failure. In this embodiment, the failure rate is determined by changing the allowable crack length Acr, and the repair criterion is set so as to minimize the total cost.

As described above, for the crack-propagation prediction method and program according to this embodiment, in the correlation-information preparing step (Step SA1 in FIG. 2), the crack length formed in the test object is measured by a plurality of inspectors using a plurality of inspection methods, and the correlation between the measured values and the actual crack length is determined; and in the crack-length estimating step (Step SA2 in FIG. 2), since the actual crack length is estimated by correcting the actual measured values from the inspection using the correlation, the precision of estimating the actual crack length can be improved. Then, in the crack-propagation-curve estimating step (Step SA3 in FIG. 2), the crack-propagation curves are estimated by setting the estimated crack length as an origin; therefore, the precision of estimating the crack-propagation curves can be improved.

In this way, it is possible to specify the numerical value range of the actual crack length with high precision. In this way, according to the present invention, the crack-propagation curves are estimated by taking into consideration the measurement error due to the differences in the inspectors and the measurement error due to the differences in the inspection methods; therefore, it is possible to specify the numerical value range of the actual crack length with a margin that is neither too large nor too small. As a result, in the repair-criterion determining step (Step SA4 in FIG. 2), an appropriate repair criterion (allowable crack length) that lowers the total cost, which is the sum of the cost of repair and the cost due to damage, such as failure, can be even more accurately set.

In this embodiment, a correlation diagram is prepared for each combination of inspector and inspection method, and the measured values from the inspection are corrected using this correlation diagram. However, this embodiment is not limited to this example, and, for example, a correlation diagram may be prepared for each inspector or inspector qualification (classification), inspection environment (natural conditions, such as temperature, the specifications of the equipment, etc.), or each inspection method, and the measured values from the inspection may be corrected using any of the correlation diagrams.

Second Embodiment

Next, a crack-propagation prediction method and program according to a second embodiment of the present invention will be described with reference to the drawings.

A crack-propagation determining apparatus according to this embodiment has the hardware configuration shown in FIG. 1 in the same manner as the first embodiment described above, and the CPU 1 realizes the crack-propagation prediction method described below by reading out and executing a crack-propagation prediction program stored in the hard disk 3.

The crack-propagation prediction method according to this embodiment predicts the time-sequential change in the length of a crack initiated in hot parts by simulating the conditions of the hot-parts used in a high-temperature environment from the beginning of use. More specifically, the simulation is for the series of time-sequential changes in which a crack is formed due to operation accompanying the start-up and stopping of a gas turbine from the time the gas-turbine hot-parts were brand new; the crack length is measured during a periodic inspection; the need for treatment, such as repair, is determined on the basis of the result; ones that are determined to require repairing are repaired; and then, operation is resumed. Moreover, a crack-propagation curve, i.e., the probability distribution of the change in the crack length with respect to the number of starts and stops, is predicted through computational simulation.

Figure 7:
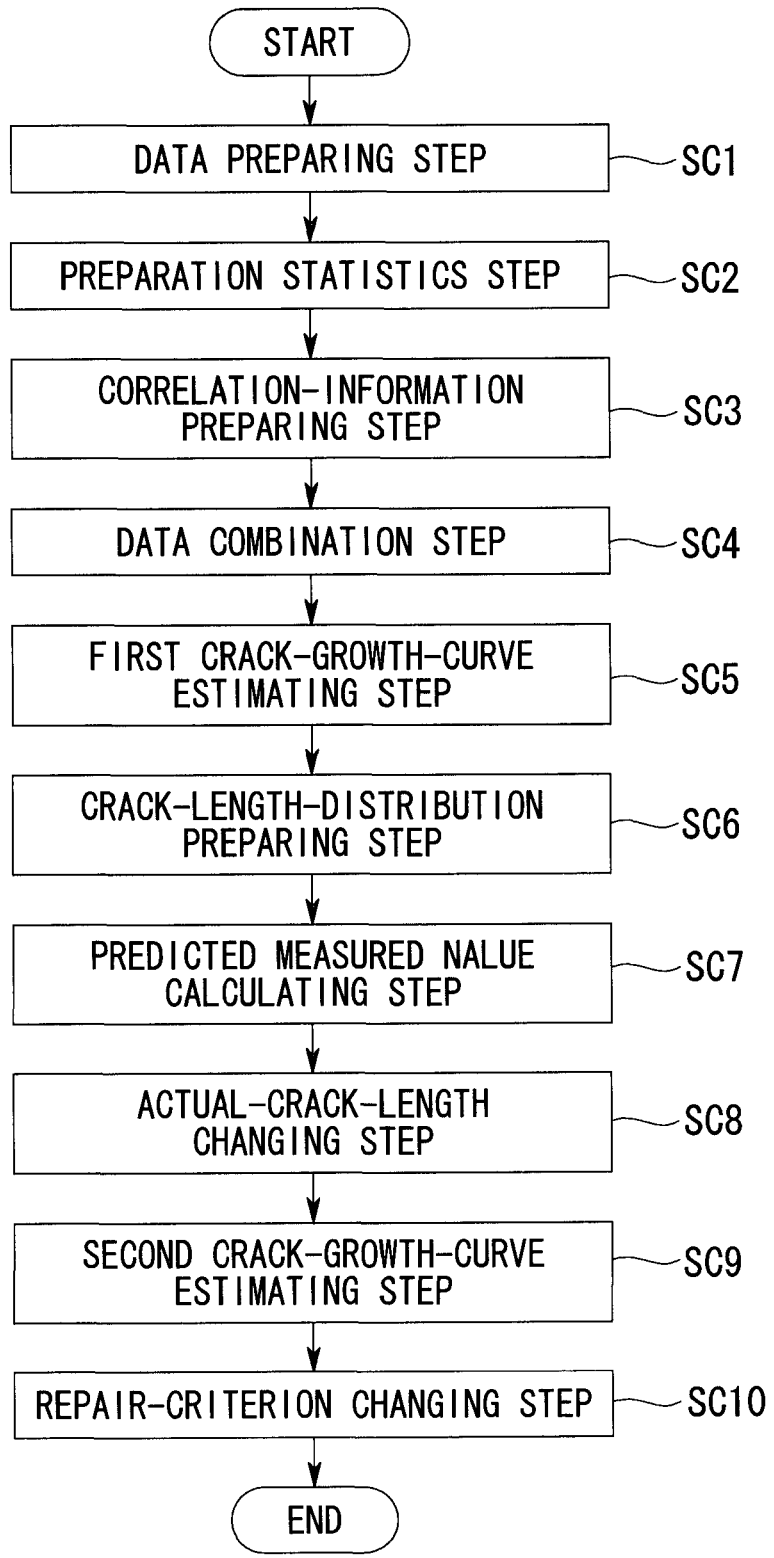
FIG. 7 is a flow chart illustrating a crack-propagation prediction method according to a second embodiment of the present invention.

The crack-propagation prediction method according to this embodiment, as shown in FIG. 7, includes a data preparing step (Step SC1 in FIG. 7) of preparing data for carrying out the Monte Carlo method on factors influencing the fatigue properties, such as crack initiation and crack propagation; a preparatory statistics step (Step SC2) of carrying out statistical processing on the prepared data; a correlation-information preparing step (Step SC3) of measuring the length of a crack initiated in hot parts or a test object used in a high-temperature environment by a plurality of inspectors or a plurality of inspection methods and determining the correlation between the measured values and the actual crack length; a data combination step (Step SC4) of preparing combinations of data for carrying out calculation by the Monte Carlo method based on data acquired in Steps SC1 to SC3; a first crack-propagation-curve estimating step (Step SC5) of determining crack-propagation curves of the respective data combinations prepared in Step SC4; a crack-length-distribution preparing step (Step SC6) of carrying out statistical processing using the crack-propagation curves and further determining a crack-length distribution at the number of starts and stops equivalent to the time of the periodic inspection; a predicted-measured-value calculating step (Step SC7) of calculating a predicted measured value by correcting the crack length determined in the first crack-propagation-curve estimating step during the inspection using the correlation acquired in Step SC3; an actual-crack-length changing step (Step SC8) of determining whether or not the predicted measured value is smaller than or equal to a predetermined repair criterion and changing the actual crack length on the basis of this determination result; a second crack-proparation-curve estimating step (Step SC9) of determining subsequent crack-propagation curves originating from the actual crack length when the predicted measured value is smaller than or equal to the repair criterion; and a repair-criterion changing step (Step SC10) of calculating the failure rate and changing the repair criterion in response to the value thereof. Each step will be described in detail below.

Data Preparing Step

This step is a step of preparing data for carrying out a probabilistic method using the Monte Carlo method on factors that influence the fatigue properties, i.e., crack initiation and propagation behavior, of a target site. Statistical processing of parameters required for predicting the temperature and stress at the target site and its vicinity is carried out. The required parameters are material property factors, boundary condition factors, and shape factors. The material property factors include heat conductivity, thermal expansion, elastic modulus, etc.; the boundary condition factors include gas pressure and gas temperature of combustion gas, heat transfer between combustion gas and surfaces of parts, gas pressure and gas temperature of cooling air, and heat transfer between the cooling air and the surfaces of parts; and the shape factors include the wall thickness of the target site. Such data may not only include experimental or analytical data acquired solely for performing the method according to the present invention but may also include conventionally accumulated data and data extracted from known documents. Furthermore, it is better that the number of data items be large for carrying out the statistical processing described below.

The data sets of these parameters are collections of raw data that are not statistically processed. The data sets are stored in respective databases (data storage devices) built into or connected to the crack-propagation prediction apparatus, and parameters required for calculation can be read out or displayed. When statistical analysis has already been carried out and probability distribution function parameters are determined, this step may be omitted, which is also the same for the preparatory statistics step (Step SC2) described below.

Next, statistical processing is carried out on raw data values, which are parameters required for calculation, stored in the databases. Here "statistical processing" includes processing for determining statistical values, such as average values and standard deviations, of the parameters and determining parameters that define a distribution function by applying the probability distribution of each parameter to an appropriate distribution function, such as a normal distribution. The results of the statistical processing are stored in the databases and are displayed on a monitor when required.

Preparatory Statistics Step

In this step, processing is carried out on parameters to predict the fatigue properties of the target part. "Fatigue properties" include properties associated with crack initiation and properties associated with crack propagation. To predict these properties, it is necessary to determine the fatigue crack initiation life and the fatigue crack propagation life. For the former, a relational expression of the stress range or the strain range and the fatigue crack initiation life is employed, and for the latter, a relational expression of the stress intensity factor range (or the cyclic J integration range) and the crack-propagation rate is employed. These expressions are derived on the basis of fatigue test data of a small test object extracted from an actual part or a material having a metal structure equivalent to the actual part.

The Manson-Coffin Equation is a known example of the relational expression of the strain range and the fatigue crack initiation life and is represented by the following Equation (1).

$$\Delta \epsilon p \times Nf^{\alpha} = Ci \quad (1)$$

In Equation (1), $\Delta \epsilon p$ represents the plastic strain range, and Nf represents the fatigue life of the test object. Here, $\alpha$ and Ci are material constants that depend on temperature and are parameters for predicting the fatigue crack initiation life. $\alpha$ and Ci may be formulated as a function of temperature, and the constants of this formula may be set as parameters for predicting the fatigue crack initiation life. The fatigue life Nf of the small test object is typically regarded as being equivalent to the crack initiation life of the actual part (for example, refer to Nihon Zairyogakkai, "kouon kyodo no kiso (basics of high-temperature strength)" p. 61, issued Oct. 20, 1999). There is also a known relational expression using stress instead of strain.

The following Equation (2) is an example of a relational expression of the stress intensity factor range and the crack-propagation rate and is known as the Paris Law.

$$da/dN = Cp \times \Delta K^m \quad (2)$$

In Equation (2), da/dN represents the crack-propagation rate, and $\Delta K$ represents the stress intensity factor range. Here, Cp and m are material constants and depend not only on temperature but also on the stress (or strain) waveform.

These material parameters $\alpha$, Ci, Cp, and m associated with fatigue properties at a specific temperature or the material constants when these parameters are represented as functions of temperature are stored in an external storage device, such as the hard disk 3 built into the crack-propagation prediction apparatus or a database (not shown) connected to the apparatus, in a similar manner to the parameters for predicting the temperature and stress in the above-described data preparing step (Step SC1). The CPU 1 carries out statistical processing using these parameters, determines the statistical parameters that are capable of representing the probability distribution function, and saves these in a database. Furthermore, the crack-propagation prediction apparatus is constructed such that the above-described material parameters, the correction coefficient, or the like can be corrected when required each time an inspection result and an investigation result of a part used for operation are acquired.

Correlation-Information Preparing Step

This step is a step of acquiring at least one of the relationship between the measured values of the crack length and the actual crack length due to the assumed differences of the inspection methods and inspectors and the relationship between the actual crack length and the defect detection probability. In this step, the procedure of acquiring the correlation between the measured values of the crack length and the actual crack length due to the differences in the inspection methods and the inspectors is the same as that in Step SA1 (see FIG. 2) according to the above-described first embodiment, and thus a description thereof is omitted. The relationship between the defect detection probability and the actual crack length will be described below.

Figure 8:
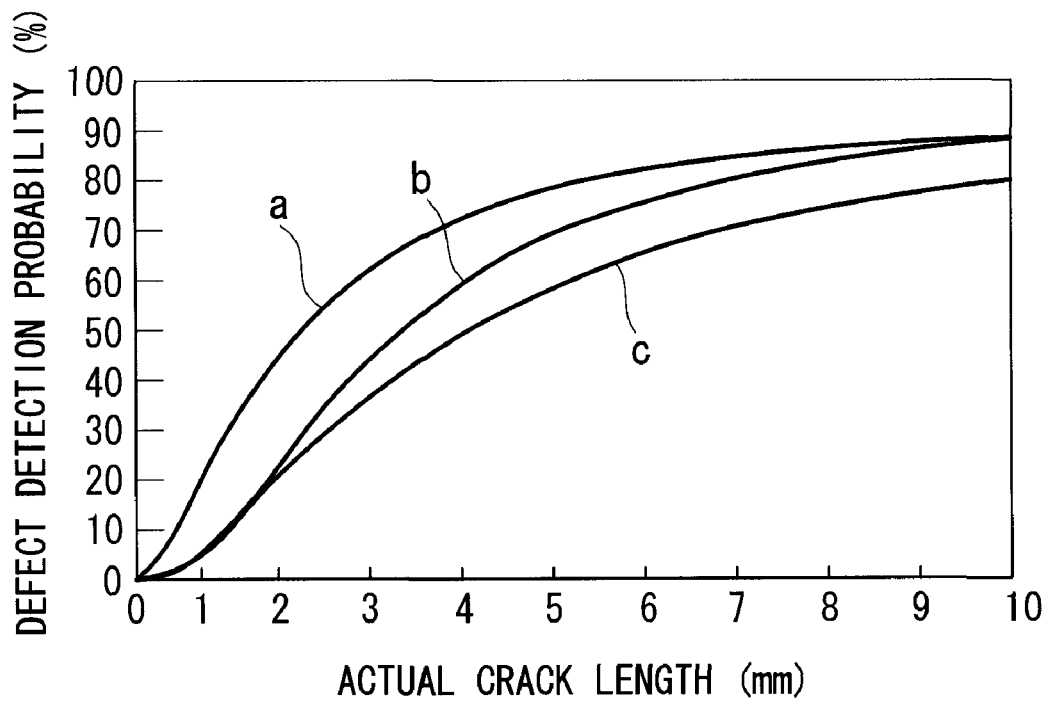
FIG. 8 illustrates the relationship between actual crack length and defect detection probability.

FIG. 8 shows the relationship between the actual crack length and the defect detection probability. Here, "defect detection probability" represents the probability of detecting a crack by each inspector with respect to an actual defect length. As shown in FIG. 8, as an overall tendency, the smaller the defect is, the higher the probability (frequency) of overlooking it is, and the defect detection probability differs depending on the inspector. For example, as shown in the drawing by solid line a, it is presumed that the defect detection probability of an experienced expert is high, and the variation in the measured values is small. On the other hand, as shown in the drawing by solid line c, the defect detection probability of a less-experienced beginner is low, and the variation in the measured values is large. Moreover, b is obtained through an inspection method different from a and c, and was obtained by the same expert as a. This shows that the defect detection probability of the same inspector varies greatly.

In this way, by measuring the test object by a plurality of inspectors having different measurement skills and acquiring these measured values as data, the reliability of the statistical processing, such as the probability distribution, subsequently carried out can be improved. When the measured crack length is zero, this does not necessarily mean that the probability of a crack existing is zero. In such a case, the existence of a crack having a certain crack length can be presumed probabilistically on the basis of the relationship between the actual crack length and the crack detection probability.

Data Combination Step

In this step, data for acquiring crack-propagation curves by employing the Monte Carlo method is prepared on the basis of the statistical processing result of each parameter acquired in the respective steps described above (Steps SC1 to SC3 in FIG. 7). The Monte Carlo method is a numerical calculation method of solving a problem through trial and error using a contingent random variable, such as random numbers, and, in some cases, is used as means for predicting statistical data including variation, such as in the present invention (for example, refer to Japanese Unexamined Patent Application, Publication No. 2005-26250).

First, to carry out statistical processing, a sufficient number of N data combinations are prepared. FIG. 9 shows an example of the prepared N combinations. However, the numerical values in the table shown in FIG. 9 are obtained by normalizing the average value and the standard deviation of each parameter on the basis of the probability distribution of the parameter, and when carrying out the calculation, it is necessary to input the average value and the standard deviation and carry out conversion. In other words, the numerical values of the parameters in the table are determined by $(X-m)/\sigma$, where the actual value is represented by X, the average value for each parameter is represented by m, and standard deviation is represented by $\sigma$.

Numerical values are randomly assigned to the parameters, such as the high-temperature gas pressure and heat conductivity, based on the probability distribution of each parameter prepared in the data preparing step (Step SC1 in FIG. 7) and the preparatory statistics step (Step SC2 in FIG. 7), and when considering all N combinations, the probability distribution is substantially the same as the probability distribution of each parameter prepared in the data preparing step and the preparatory statistics step (here, an example is a normal distribution).

Here, it is "substantially" the same because the values actually used are discretized numerical values and are not exactly the same. As a result, for parameters that have less influence on the fatigue properties, a smaller number of numerical values may be used taking into consideration the time required for calculation. Moreover, two parameters within the same combination that do not have any correlation, such as high-temperature gas pressure, elastic modulus, and wall thickness, vary independently of each other.

The material property values depend on temperature, and the temperature of the target site differs due to a variation in the environmental factors for each combination; therefore, it is preferable, from the viewpoint of reliability, to display the material property parameters as a function with temperature set as a variable. However, when a parameter has a small dependency on temperature or when the resulting variation in the temperature of the target site is small, the parameter may be one that does not depend on temperature for the purpose of shortening the calculation time. FIG. 9, illustrated as an example, shows values calculated on the assumption that the variation in the temperature of the target site is small. The prepared N combinations of data are temporarily stored in the hard disk 3 or the external storage device.

First Crack-Propagation-Curve Estimating Step

In this step, the N combinations of data prepared in the data combination step are input to obtain N crack-propagation curves. Specifically, data of the material property factors, boundary condition factors, and shape factors for the first combination is input or read out, thermal/stress analysis is carried out, and the temperature distribution and stress distribution of the target site of the part are determined. Using the acquired temperature distribution and stress distribution, parameters for predicting the fatigue property are input or read out, and then, at first, the number of starts and stops at which a crack forms is determined by, for example, the above-mentioned Manson-Coffin Equation.

Next, the acquired temperature distribution and stress distribution, and the operating conditions of the gas turbine are input; parameters, such as stress, temperature, and material constants, which are determined in the preparatory statistics step, are substituted into the above-mentioned equation of crack-propagation rate; and, using the equation of crack-propagation rate, the relationship between the number of starts and stops after crack initiation and the crack length is determined by, for example, a differential method.

Figure 10:
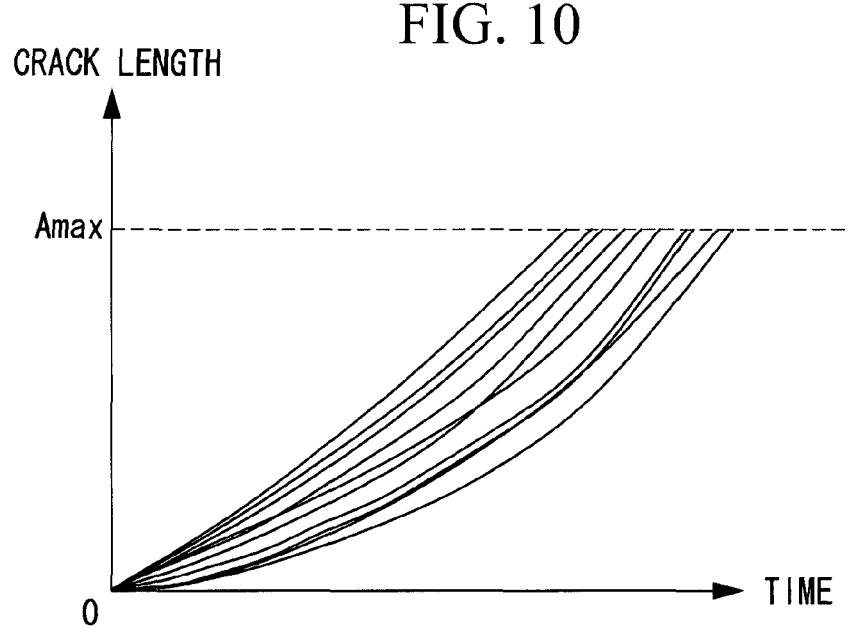
FIG. 10 illustrates N crack-propagation curves acquired in a first crack-propagation-curve estimating step.

The calculation proceeds, and then the calculation ends upon acquisition of the crack-propagation curve for the first combination when the crack length reaches the limit crack length Amax, which is stored separately in advance in the hard disk 3; and this crack-propagation curve is displayed on the monitor 5 (see FIG. 1) and stored in the database or the like. Subsequently, the data of the second combination is used to acquire a crack-propagation curve of the second combination through the same procedure as that described above. Calculation is repeated in this way to acquire N crack-propagation curves. The acquired curves are displayed on the monitor 5. FIG. 10 is a diagram illustrating an example of the N crack-propagation curves displayed on the monitor 5.

The limit crack length Amax, which is the end point of the crack-propagation curve, is a limit length at which a part does not lose its function so long as the length is smaller than or equal to this limit length, and is determined on the basis of the design so long as there is no possibility of scattering of parts, etc.; therefore, it may be a definite value that does not include any variation.

However, when the limit crack length Amax is defined on the basis of a concept that it is determined by, for example, an onset limit for low-stress, high-cycle fatigue crack propagation due to resonance, vibratory stress due to resonance and a threshold stress intensity factor range ($\Delta Kth$) are set as contingent random variables, and, on the basis thereof, the failure-limit crack length may be determined as a parameter.

Crack-Length-Distribution Preparing Step

In this step, the probability distribution of the fatigue crack length is determined by carrying out statistical processing using the N crack-propagation curves obtained in the first crack-propagation-curve estimating step. Here, "probability distribution" is a probability distribution of the number of starts and stops at which the crack reaches a specific length or a probability distribution of the crack length at a specific number of starts and stops, where the specific crack length and the specific number of starts and stops may be determined depending on the purpose of use. Here, considering the objective of this embodiment, the length at the number of starts and stops equivalent to the time of a periodic inspection is used.

Predicted-Measured-Value Calculating Step

Figure 11:
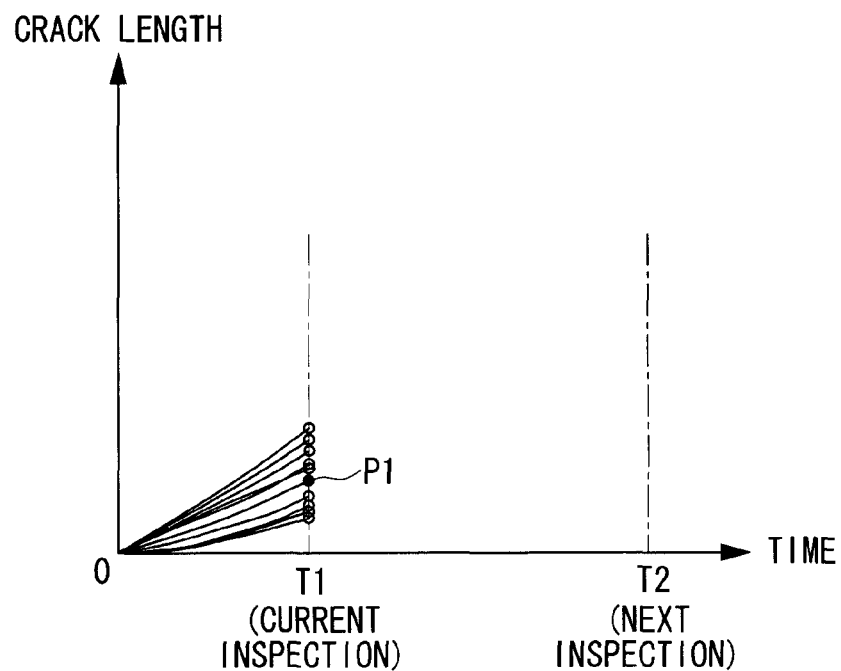
FIG. 11 illustrates a predicted measured value calculating step.

In this step, a predicted measured value is calculated by correcting the crack length at the number of starts and stops equivalent to the time of the first periodic inspection (T1 in FIG. 11) using the correlation prepared in the correlation-information preparing step (Step SC3 in FIG. 7). For example, each crack-propagation curve obtained in the above-described first crack-propagation-curve estimating step is regarded as the actual crack length. In other words, it is a value that does not include the measurement error due to the inspectors, inspection methods, etc., and whether or not the hot-parts will fail is determined based on the actual crack length.

On the other hand, when considering an actual inspection, as described above, the measured values include error due to the inspectors and inspection methods. In an actual inspection, it is determined whether or not the hot-parts should be repaired depending on the values measured by the inspectors. The measured values including error are important parameters for simulating the time-sequential conditional changes in the hot-parts.

The actual crack lengths (N items) that do not include error are already determined in the above-described first crack-propagation-curve estimating step (Step SC5 in FIG. 7); therefore in this step, the measured values obtained during the inspection for the actual crack lengths (N items) are predicted by including error based on the correlation diagram. Here, one crack length P1 of the N actual crack lengths shown in FIG. 11 will be described as a representative example in this step.

Figure 12:
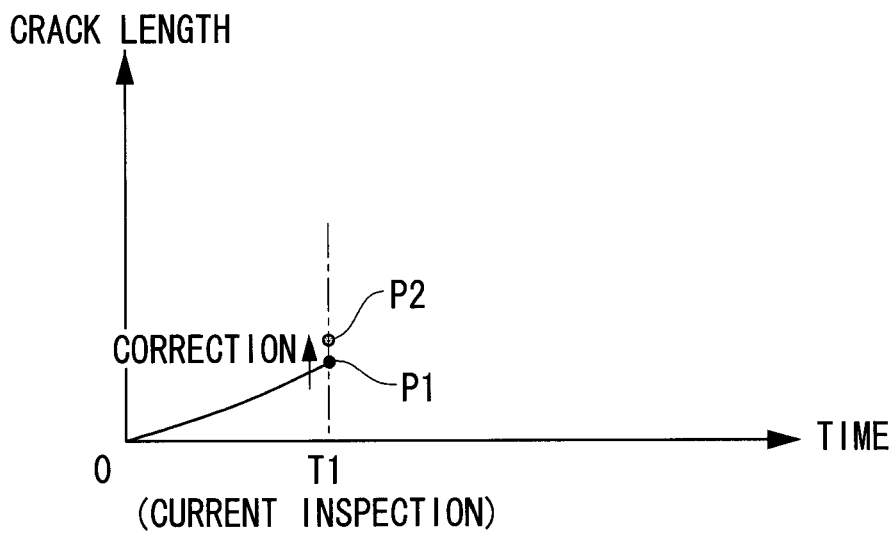
FIG. 12 illustrates the predicted-measured-value calculating step.

As shown in FIG. 12, a predicted measured value P2 is calculated by using the correlation diagram (see FIG. 4) to correct the actual crack length P1 for the first inspection (T1) among the crack-propagation curves acquired during the first crack-propagation-curve estimating step. This is accomplished by, for example, determining the probability distribution from the correlation diagram and correcting the actual crack length on the basis of this probability distribution. This simulates a situation in which an inspector acquires P2 as the measured value of a crack whose actual crack length is P1. Here, the measured value is a definite value. Instead, however, it may be represented by a probability distribution corresponding to the variation in the correlation diagram (variation in the measured values of the same actual crack length).

Actual-Crack-Length Changing Step

In this step, it is determined whether or not the predicted measured value calculated in the predicted-measured-value calculating step is smaller than or equal to the predetermined repair criterion, and the actual crack length is changed in response to this determination result. For example, this is a step for making the simulation as close as possible to the actual inspection. For example, in an actual inspection, when the crack length measured by an inspector is larger than the repair criterion (allowable crack length), a repair operation for removing the crack by welding, grinding, etc. will be carried out. By carrying out the repair operation, the existing crack is reduced in size or removed.

Figure 13:
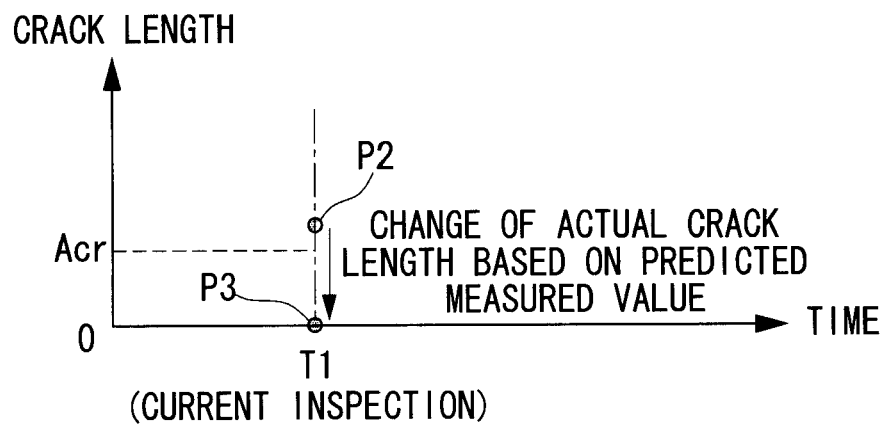
FIG. 13 illustrates an actual-crack-length changing step.
Figure 14:
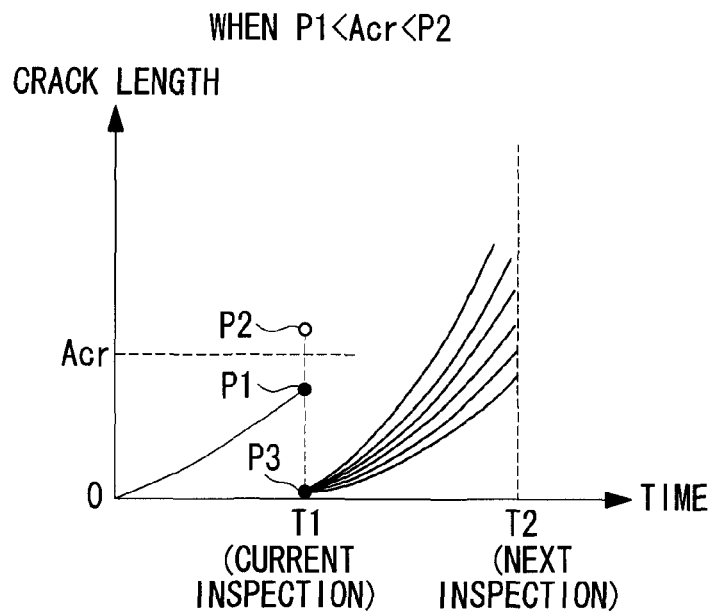
FIG. 14 illustrates the actual-crack-length changing step and a second crack-propagation-curve estimating step.
Figure 15:
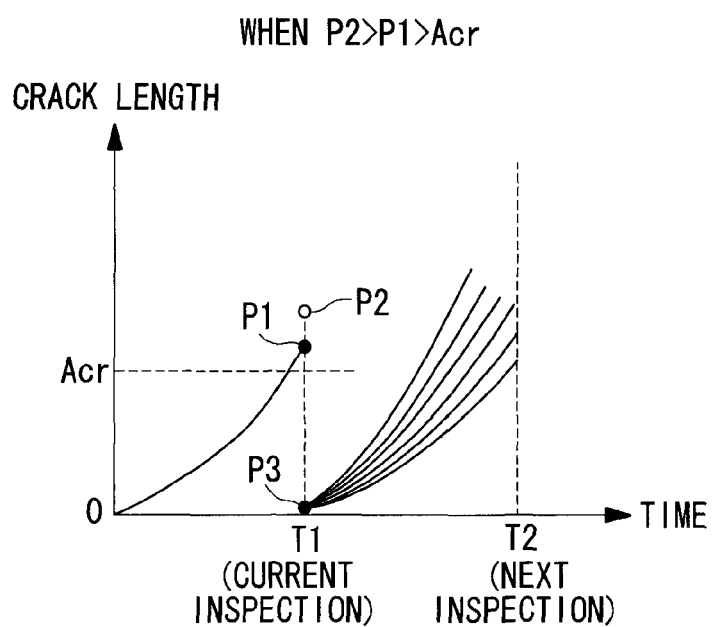
FIG. 15 illustrates the actual-crack-length changing step and the second crack-propagation-curve estimating step.

Accordingly, in this step, as shown in FIG. 13, when the predicted measured value P2 is larger than the allowable crack length Acr, it is deemed that the repair operation, etc. should be carried out, and the predicted measured value P2 is changed to zero or a value P3 that is smaller than the current value. At this time, since the crack length P1 is also reduced by repair, for example, as shown in FIGS. 14 and 15, the actual crack length P1 is changed to a value that is the same as the value P3 after repair. However, when it is known after repair that the value differs from how it visibly appears (when a crack that is not detected visibly by an actual investigation, such as cutting, and is partially left without being repaired), P3 may be calculated from P1 on the basis of the associated data.

Figure 16:
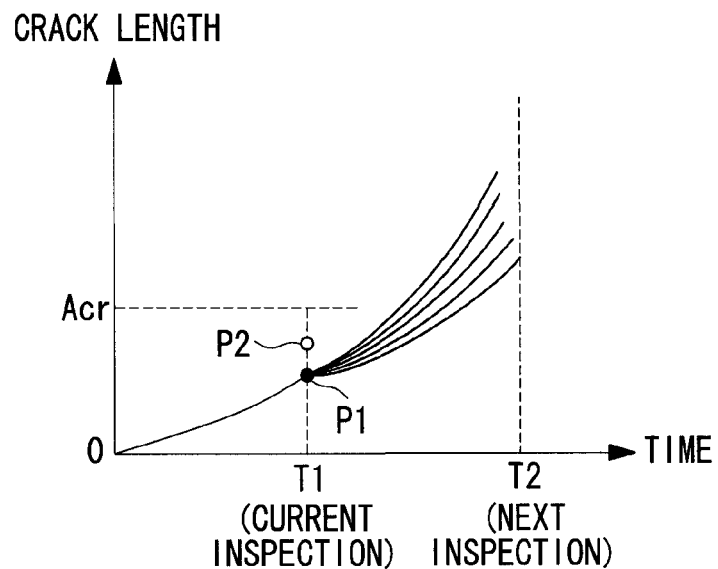
FIG. 16 illustrates the actual-crack-length changing step and the second crack-propagation-curve estimating step.
Figure 17:
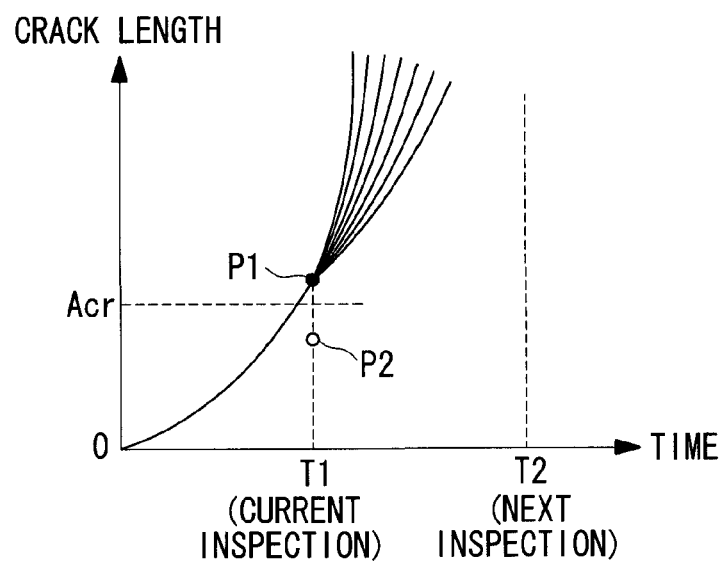
FIG. 17 illustrates the actual-crack-length changing step and the second crack-propagation-curve estimating step.

When the predicted measured value P2 is smaller than or equal to the repair criterion Acr, the predicted measured value P2 is not changed, regardless of the value of the actual crack length, and the subsequent steps are carried out on the basis of the current value, i.e., the actual crack length P1. FIGS. 16 and 17 illustrate representative cases.

In the actual-crack-length changing step, it may be determined whether or not to change the actual crack length on the basis of the correlation between the actual crack length and the detection probability prepared in the correlation-information preparing step. For example, depending on the inspector, it is possible that a large crack will be overlooked. For example, in the graph illustrated in FIG. 8, when a 2-mm crack is formed, inspector A discovers this crack 55% of the time and overlooks it 45% of the time. In this way, the predicted measured value may be set by determining, using a probability distribution, etc., whether or not a crack will be detected or, if detected, how much error the measured value will include, depending on the inspector and the actual crack length.

Second Crack-Propagation-Curve Estimating Step

In this step, when the actual crack length is not changed in a predicted-measured-value calculating step, crack-propagation curves originating from the current value P1 are calculated (See FIG. 14). The calculation method is the same that in the above-described first crack-propagation-curve estimating step. At this time, the material may be changed to simulate welding repair. Specifically, the parameters of the crack-propagation rate and the parameters of the equation of fatigue crack initiation life may be changed. Crack-propagation calculation is carried out until the number of starts and stops equivalent to the time of the next periodic inspection is reached; the processing returns to the predicted-measured-value calculating step when inspection time is reached; and the subsequent processing is repeated. Instead, the processing may be carried out until the crack length reaches the limit crack length Amax.

In the actual-crack-length changing step, when the actual crack length is changed to zero, this means no cracks are formed. In such a case, simulation is carried out until a crack forms in an area without cracks, and then the degree of propagation of the formed crack is estimated. In FIG. 10, the time period before formation is omitted for simplification.

In the predicted-measured-value calculating step, the actual-crack-length changing step, and the second crack-propagation-curve estimating step, the actual crack length P1 is described as an example; however, by carrying out the steps for each of the N crack lengths (see FIG. 11), it is possible to predict the crack propagation condition while taking into consideration various factors.

Repair-Criterion Changing Step

The objective of this step is to appropriately revise the repair criterion such as to minimize the overall cost of damage and repair. The overall cost is illustrated in FIG. 18 and will be described below.

By completing all of the above-described steps and determining the crack-propagation curve for each combination, ones that may fail (the crack length reaching the allowable crack length) before the next periodic inspection are determined. The probability of failure (failure rate) by the time equivalent to the next periodic inspection is determined by determining the ratio of the crack-propagation curves. By determining the repair criterion and the failure rate on the basis of the repair criterion, the overall cost can be calculated. Thus, by changing the repair criterion and determining the overall cost at that time, a repair criterion that minimizes the overall cost can be determined. Specifically, the processing is repeated for resetting the repair criterion (allowable crack length) referred to in the predicted-measured-value calculating step, correcting the crack lengths on the basis of FIGS. 14 to 17, if required (SC8), and carrying out the second crack-propagation-curve estimating step (SC9). By repeating such processing several times, the relationship between the repair criterion and the failure rate is determined, and the relationship between the repair criterion and the overall cost is determined.

Here, the relationship between the failure rate and cost will be described. In order to reduce the number of parts that fail by the next periodic inspection and simultaneously decrease the frequency of failure, it is necessary to set the repair criterion to a small value. However, at the same time, the smaller the repair criterion, the larger the cost (hereinafter referred to as "cost of repair"), such as material cost and labor cost, required for repair and replacement due to discarding.

Therefore, in this step, as shown in FIG. 18, an optimal repair criterion for minimizing the overall cost is determined. Here, "the overall cost" is the sum of the cost of repair and the cost of failure, which are described above. The cost of repair is the repair expenses caused by failure in other parts and devices and damage due to halted operation associated with the repair and includes costs associated with damage to business operations. The cost due to failure is determined by multiplying the actual damage cost by the probability of failure. If the repair criterion is large, the probability of failure increases, and thus the cost due to the failure becomes large even if the damage cost is the same.

Since the overall cost is regarded as the sum of the repair cost and the product of the cost generated by failure, such as fracture (due to not carrying out repair), and the probability of its occurrence, it is possible to calculate the overall cost using a function of the repair criterion.

As described above, with the crack-propagation prediction method and program according to this embodiment, the length of a crack initiated in a test object is measured by a plurality of inspectors or a plurality of inspection methods; the correlation between the measured values and the actual crack length is determined; and the predicted measured value is estimated by correcting the actual crack length of the inspection acquired through simulation using this correlation; therefore, the predicted measured value can be set close to the measured values by the inspector during an actual inspection. Then, the predicted measured value obtained during the inspection is changed depending on whether or not the predicted measured value is smaller than or equal to the repair criterion; therefore, it is possible to carry out simulation according to actual operation.

In this way, since the predicted measured value is estimated by taking into consideration the measurement error due to the differences among the inspectors and the measurement error due to the difference in the inspection methods, it is possible to improve the simulation precision. Moreover, by calculating the repair cost, etc. using the result of a simulation carried out at high precision, a repair criterion capable of minimizing costs can be determined with superior precision.

The embodiments of the present invention have been described in detail above with reference to the drawings. However, the detailed structure is not limited to these embodiments and may include various design modifications within the scope of the present invention.

For example, the above-described steps may be carried out manually using a terminal of a large-scale computer or a computing device, such as a personal computer, as shown in FIG. 1. However, it is also possible to automatically acquire a final repair criterion through batch processing by inputting the various costs and cost calculation formulas, which depend on a person's judgment in advance.

Furthermore, it is efficient to connect the above-described crack-propagation prediction apparatus and an in-house LAN or an Internet connection, to make it possible to obtain data from various experimental databases and databases of other organizations.

In the embodiments, high-temperature equipment, such as gas turbine parts, used in a high-temperature environment is described. However, the present invention can be applied to crack-propagation behavior associated with structural bodies and parts used in normal room-temperature or low-temperature environments and to processing of the results by inspectors.

The invention claimed is:

1. A crack-propagation prediction method comprising:
a correlation-information preparing step of measuring the length of a crack initiated in a test object by a plurality of inspectors and/or a plurality of inspection methods and obtaining correlation information between data acquired through the measurement and the condition of an actual crack;
a crack-length estimating step of estimating the actual length of a crack initiated in an inspection target on the basis of the crack length measured by an inspector during inspection of the inspection target and the correlation information; and
a crack-propagation-curve estimating step of estimating a crack-propagation curve of the inspection target originating from the crack length estimated in the crack-length estimating step.

2. The crack-propagation prediction method according to claim 1, wherein in the crack-propagation-curve estimating step, some or all parameters determining a crack initiation life and a crack-propagation rate for determining the relationship between the number of starts and stops after the inspection and the crack length are set to random variables, and the crack-propagation curve is probabilistically predicted using a Monte Carlo Method.

3. The crack-propagation prediction method according to claim 1, wherein
in the correlation-information preparing step, the correlation information is prepared for each of the inspection methods and/or each measuring ability level of the inspectors, and
in the crack-length estimating step, the actual crack length is estimated using the correlation information corresponding to the inspection method used during the inspection and/or the measuring ability of the inspector who carried out the measurement during the inspection.

4. A crack-propagation prediction method for predicting a time-sequential change in the length of a crack initiated in an inspection target by simulating the conditions of the inspection target from the beginning of use, the method comprising:
a first crack-propagation-curve estimating step of estimating a crack-propagation curve from the beginning of use of the inspection target;
a correlation-information preparing step of measuring the length of the crack initiated in a test object by a plurality of inspectors or a plurality of inspection methods and obtaining correlation information between data acquired through the measurement and the condition of an actual crack;
a predicted-measured-value calculating step of calculating a predicted measured value by using the correlation information to correct an actual crack length obtained during inspection predicted in the first crack-propagation-curve estimating step; and
an actual-crack-length changing step of determining whether or not the predicted measured value is equal to or smaller than a repair criterion set in advance and changing, in response to the determination result, the actual crack length obtained during the inspection.

5. The crack-propagation prediction method according to claim 4, wherein in the actual-crack-length changing step, when the predicted measured value obtained during the inspection exceeds the repair criterion, the crack is to be repaired, and the actual crack length is changed to a value equal to zero or smaller than the original length.

6. The crack-propagation prediction method according to claim 4, further comprising:
a second crack-propagation-curve estimating step of estimating a crack-propagation curve originating from the actual crack length when the predicted measured value is equal to or smaller than the repair criterion.

7. The crack-propagation prediction method according to claim 6, wherein in at least one of the first crack-propagation-curve estimating step and the second crack-propagation-curve estimating step, some or all parameters determining a crack initiation life and a crack-propagation rate for determining the relationship between the number of starts and stops and the crack length are set to random variables, and the crack-propagation curve is probabilistically predicted using a Monte Carlo Method.

8. A crack-propagation prediction program causing a computer to execute:
a step of obtaining correlation information between data of the length of a crack initiated in a test object measured by a plurality of inspectors and/or a plurality of inspection methods and an actual crack length;
a step of estimating the actual length of a crack initiated in an inspection target on the basis of the crack length measured by an inspector during inspection of the inspection target and the correlation information; and
a step of estimating a crack-propagation curve of the inspection target originating from the estimated crack length.

9. A crack-propagation prediction program for predicting a time-sequential change in the length of a crack initiated in an inspection target by simulating the conditions of the inspection target from the beginning of use, the program causing a computer to execute:
a step of estimating a crack-propagation curve from the beginning of use of the inspection target;
a step of obtaining correlation information between data of the length of a crack initiated in a test object measured by a plurality of inspectors and/or a plurality of inspection methods and an actual crack length;
a step of calculating a predicted measured value by correcting an actual crack length in the inspection target obtained during inspection predicted in the step of estimating a crack-propagation curve, using the correlation information; and
a step of determining whether or not the predicted measured value is equal to or smaller than a repair criterion set in advance and changing the actual crack length obtained during the inspection in response to the determination result.

* * * * *